(12) United States Patent
Elsome et al.

(10) Patent No.: US 7,153,532 B1
(45) Date of Patent: Dec. 26, 2006

(54) SENSING GASEOUS SUBSTANCES USING METAL COMPLEXES

(75) Inventors: Amanda Maria Elsome, Henley (GB); Elizabeth Slade, Kingston Upon Thames (GB)

(73) Assignee: Johnson Matthey Public Limited Company, London (GB)

( * ) Notice: Subject to any disclaimer, the term of this patent is extended or adjusted under 35 U.S.C. 154(b) by 0 days.

(21) Appl. No.: 09/763,981

(22) PCT Filed: Aug. 25, 1999

(86) PCT No.: PCT/GB99/02803

§ 371 (c)(1),
(2), (4) Date: May 23, 2001

(87) PCT Pub. No.: WO00/13009

PCT Pub. Date: Mar. 9, 2000

(30) Foreign Application Priority Data

Aug. 28, 1998 (GB) .................................... 9818766

(51) Int. Cl.
*G01N 21/75* (2006.01)
*G01N 21/78* (2006.01)
*G01N 21/84* (2006.01)

(52) U.S. Cl. ...................... 426/232; 426/87; 426/112; 426/231; 436/20; 436/172; 436/3; 116/206; 422/86; 422/58

(58) Field of Classification Search .................. 426/87, 426/112, 231, 232; 422/82.08, 82.07, 56, 422/57, 58, 61, 52, 86–87; 436/20, 172, 436/1, 2, 164, 21–24; 116/206
See application file for complete search history.

(56) References Cited

U.S. PATENT DOCUMENTS

| | | | |
|---|---|---|---|
| 4,285,697 A | 8/1981 | Neary | |
| 4,746,616 A | 5/1988 | Honigs et al. | |
| 4,772,707 A | 9/1988 | Hamon et al. | |
| 5,030,420 A * | 7/1991 | Bacon et al. | 422/82.07 |
| 5,053,339 A | 10/1991 | Patel | |
| 5,058,088 A | 10/1991 | Haas et al. | |
| 5,064,576 A * | 11/1991 | Suto | 556/37 |
| 5,096,724 A | 3/1992 | Zenner et al. | |
| 5,244,813 A * | 9/1993 | Walt et al. | 436/172 |
| 5,306,466 A * | 4/1994 | Goldsmith | 422/58 |
| 5,319,975 A | 6/1994 | Pederson et al. | |
| 5,407,829 A * | 4/1995 | Wolfbeis et al. | 436/1 |
| 5,501,945 A * | 3/1996 | Kanakkanatt | 430/338 |
| 5,512,490 A * | 4/1996 | Walt et al. | 436/171 |
| 5,599,913 A * | 2/1997 | Harris et al. | 534/856 |
| 5,653,941 A | 8/1997 | Veretto et al. | |
| 5,699,326 A | 12/1997 | Haas et al. | |
| 5,753,285 A * | 5/1998 | Horan | 426/87 |
| 5,822,280 A | 10/1998 | Haas | |
| 5,834,626 A * | 11/1998 | De Castro et al. | 73/23.3 |
| 5,869,341 A | 2/1999 | Woodaman | |
| 5,930,206 A | 7/1999 | Haas et al. | |
| 5,976,827 A * | 11/1999 | Jeffrey et al. | 435/34 |
| 6,149,952 A * | 11/2000 | Horan | 426/87 |
| 6,285,282 B1 | 9/2001 | Dorenbosch et al. | |
| 6,294,997 B1 | 9/2001 | Paratore et al. | |
| 6,428,748 B1 | 8/2002 | Wallach | |
| 6,495,368 B1 * | 12/2002 | Wallach | 436/20 |
| 6,576,474 B1 | 6/2003 | Wallach | |

FOREIGN PATENT DOCUMENTS

| | | |
|---|---|---|
| DE | 43 32 512 | 3/1995 |
| DE | 196 05 522 | 8/1997 |
| EP | 0 449 798 | 10/1991 |
| JP | 59-087364 | 5/1984 |
| JP | 60-035260 | 2/1985 |
| JP | 60-063464 | 4/1985 |
| JP | 60-063465 | 4/1985 |
| JP | 5-34349 | 2/1993 |
| JP | 93-010624 | 2/1993 |
| WO | 93/15403 | 8/1993 |
| WO | WO 95/23872 | 9/1995 |
| WO | WO 95/33991 | 12/1995 |
| WO | WO97/33177 * | 9/1997 |
| WO | WO 98/20337 | 5/1998 |
| WO | WO 99/59431 | 11/1999 |
| WO | WO 01/48680 A1 | 7/2001 |
| WO | WO 01/64430 A1 | 9/2001 |
| WO | WO 01/77667 A2 | 10/2001 |
| WO | WO 02/17281 A1 | 9/2002 |

OTHER PUBLICATIONS

Safety Data for Calcein, http://alergies.about.com/library/chem/blmsds-calcein.htm.*
Dojindo Molecular Technologies, Bulk Supply, p. 8, http://www.dojindo.com/bulk/bulkoffer.html.*
Wheeler, Sensor Reveals Steak Freshness, Oct. 1997, Photonics Technology World, posted at http://www.photonics.com.*

(Continued)

*Primary Examiner*—Keith Hendricks
*Assistant Examiner*—Kelly Mahafkey
(74) *Attorney, Agent, or Firm*—RatnerPrestia

(57) ABSTRACT

A metal co-ordinated complex in a medium, e.g. a palladium-fluorophore, may be used to detect food spoilage products by the release of a detectable component by preferential binding of the metal to, for example, sulphur compounds or amines. It can be easy to detect food spoilage in sealed packs.

38 Claims, No Drawings

OTHER PUBLICATIONS

Werkhoven-Goewie et al., Liquid Chromatographic Detector for Organosulphur Componds Based on a Ligand-Exchange Reaction, Jan. 9, 1981, Journal of Chromatography, 203, Abstract.*

British Search Report dated Oct. 21, 1998.

International Search Report dated Jan. 18, 2000.

Frei, R. W. and Mallet V., "Quantitative Thin-layer Chromatography of Organothiophosphorus Pesticides by *in situ* Fluorimetry," *Int. J. Environ. Chem.*, (1971), 1 (2), pp. 99-111.

Moretti, G.; Amici, M.; Cammarata, P.; and Fracassi, F., "Identification of thyrostatic drug residues in animal thyroids by high-performance thin-layer chromatography and fluorescence reaction detection," *Journal of Chromatography*, 442 (1988), pp. 459-463.

Choi, Ming Fat and Hawkins, Peter, "The development of optical chemical sensors for the detection of volatile compounds from spoiled hams," *Sensors and Actuators B*, 38-39 (1997), pp. 390-394.

Frei, Roland W.; Maclellan, Brian L.; and MacNeil, James D., "The determination of organo-sulfur compounds by thin-layer chromatography via a ligand-exchange process," *Analytica Chimica Acta*, 66 (1973), pp. 139-142.

* cited by examiner

SENSING GASEOUS SUBSTANCES USING METAL COMPLEXES

This application is the U.S. national-phase application of PCT International Application No. PCT/GB99/02803.

The present invention concerns improvements in sensors, and more particularly concerns improvements in sensors for detecting microbial food spoilage.

Microbial spoilage of foods is a major concern to food producers, retailers and consumers. Consumers may perceive spoilage as a deterioration in taste, appearance, smell and/or texture, and there are clear health risks too. Currently, there is no direct in-pack measurement of food spoilage. Producers/retailers use "best before" and "use by" dates as an indication of food quality and safety. However, these methods are merely a prediction of food quality and are not a real measurement of food quality.

Food can spoil by a number of processes, including lipid oxidation, enzymatic degradation and microbial growth. The relative importance of these food spoilage processes vary from food to food, according to its constitution, handling history, and other factors. Microbial growth, however, is a major spoilage factor.

There are many methods currently used to determine food quality, eg organoleptic tests, standard microbiological techniques and spectroscopic analysis. None of these techniques are currently suitable for use in-pack, and may have other disadvantages such as long evaluation times and sample destruction. Accordingly, there is a need for a technique which can continuously monitor food quality in-pack, from packaging to consumption.

It has been proposed to use a fluorophore chelated with manganese for the quantitative detection of S-containing pesticides (Int. J. Environ. Chem. (1971), 1 (2), 99–111). Also, the fluorophore calcein has been described as being complexed with palladium with added zinc, to detect organo-sulphur drug residue compounds in chromatography techniques (J. Chromat. 442 (1988) 459–463) in which the compounds are spotted onto thin layer chromatography plates.

It has also been suggested that the concentration of sulphur-containing vapours from dry-cured hams could be detected by the quenching of fluorescence in tetraotylammonium fluorescein mercuric acetate (Sensors and Actuators B 38–39 (1997) 390–394). However, such a sensor compound would never be acceptable for use inside food packaging. Further, we believe that it would be more desirable for retailers to be able to detect spoilage by detecting the appearance of fluorescence or the appearance of a chromophore than by detecting the quenching of fluorescence.

Microbial growth on food and chemical degradation tends to result in the formation of volatile spoilage products. We have invented a product and method which utilises such spoilage products within the pack to sense food spoilage. Although the present invention will be described hereinafter with particular reference to food spoilage, it should be understood that its principles may be more widely applied. Thus it is contemplated that the invention may be applied to detecting the opening or the compromise of sterile packaging of instruments, dressings or drugs, in the microelectronics industry, as an aid to the quality assurance process in food factories, and in security packaging for papers, securities, banknotes, and other valuables.

The present invention provides a sensor for detecting food spoilage or the opening or compromise of packaging, comprising a metal co-ordinated complex immobilised in or on a substrate, which complex is capable of releasing a detectable component by the preferential binding of a gaseous substance to the metal of said complex. The complex may be, for example, a metal complexed with a chromophore or fluorophore, which undergoes ligand exchange with sulphur compounds (eg sulphides) or nitrogen compounds (eg amines), thus releasing the chromophore or fluorophore to indicate spoilage. Other gases relevant to the present invention contain alcohol or carbonyl groups or contain phosphorus.

Desirably, the complex is immobilised in the form of a film, which may be formed by printing, casting, roller application, brushing, spraying or like techniques, a composition comprising the complex onto the internal surface of the food package. In another embodiment, the complex is incorporated into, or into part of, a food packaging material itself. The invention therefore also provides such a composition for application onto food packaging, comprising the complex, an immobilising resin and a liquid vehicle. The system used for immobilising the complex may also retain and immobilise the chromophore or fluorophore. If required it is possible to incorporate some form of barrier layer or coating which is permeable to the food spoilage products but not to the indicator molecule or metal compounds.

A variety of metals may be used to form the complex, and include especially palladium, platinum, ruthenium or iron, but other metals may be considered, such as copper, nickel, zinc, gold, the rare earth metals, cobalt, iridium, titanium and vanadium.

Some retailers may desire that the complex releases a fluorophore which does not show any appreciable colour change under normal shop lighting, but fluoresces strongly when excited by non-visible light such as UV. This permits the retailer to scan packages, eg by a portable UV lamp, and remove those that show release of the fluorophore caused by food spoilage products. For other areas of use, release of a chromophore, giving a visible colour change, may be more desirable. A variation on release of a fluorophore is the reaction of the complex to cause a shift in the position of an emission peak. This may be sufficient to be visible by eye when the fluorophore is excited, but the invention also encompasses the detection of such a shift by an instrument. It is to be understood that the term "chromophore" as used in the present invention includes compounds which exhibit phosphorescence.

The release of the chromophore or fluorophore is desirably not specific to any type or species of microorganism. The invention is believed to be sufficiently flexible to permit the development of a variety of sensors, either which indicate directly the level of microorganism growth or which switch "on" at a given level; for example a strip of sensors may indicate increasing levels of contamination up to a danger level.

Desirably, the complex also may be designed for particular uses, and to achieve particular results. For example, a particular palladium-fluorophore complex exhibits very much faster kinetics for fluorophore release than the corresponding platinum-fluorophore complex. According to the intended use and the preferred kinetics either, or both, complexes may be used to yield particular preferred results. The complexing ligand is not itself critical providing it is released from the metal in the appropriate time-frame, and provides on reaction with spoilage products the desired fluorescence or colour change characteristics. A preferred ligand is Fluorexon, of general formula

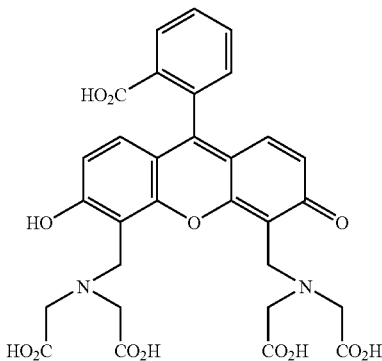

This may be reacted with Na$_2$[PdCl$_4$] to yield a Pd-Fluorexon complex which is pink in colour but which fluoresces strongly when the ligand is released. The Fluorexon molecule can itself be modified so that it is no longer water soluble, but is soluble in lipids or organic solvents, for example by using a non-co-ordinating counterion or by changes in functional groups, as is well known to the skilled chemist. The preparation of such a palladium complex is desired in more detail in the following Example.

Other palladium complexes may be considered for use in the present invention are known from the literature, for example palladium dialyzarin red, (NBu$_4$)$_2$[PdAlizarin$_2$] and the palladium complex of alizarin complexone. Generally, the complex may be any suitable complex of a dye, a complexone, a Schiff base, or could be a rare earth polyamino carboxylate. Particular complexing fluorophores to be considered in addition to Fluorexon are know per se, and include a number of compounds commercially available, such as fluorescein isothiocyanate, fluorescein, fluoresceinamine, calcein blue, "Fura 2", quinzarin, alizarin complexone, alizarin red and alizarin, isocein, "Quin 2" and 4,4-dihydroxy-azobenzene 3,3-dicarboxylic acid, disodium salt.

The presently preferred Pd-Fluorexon complex may be dissolved in an aqueous PVA solution, to form a composition which can be applied to plastics packaging materials to yield a water-insoluble film. It is envisaged that other such compositions, with other metal complexes, may be established by trial and error, and it is convenient to use generally available ink-forming technology. Such an ink may be applied to the inner surface of a package, or printed or otherwise applied onto a label for insertion into a package. Such inks or compositions may contain other components, including particularly one or more of driers, plasticisers, fillers, surfactants and pigments. In addition to labels to be packaged inside packaging, the invention includes adhesive labels, decals and the like.

Alternatively, incorporation of the complex into the packaging material may be considered, providing that when so incorporated, there is sufficient permeability to cause the complex to release the desired detectable component.

The present invention will now be described by way of example only.

EXAMPLE 1

A. Preparation of Solution of Pd:Fluorexon

4'5'-Bis(N,N-bis(caboxymethyl)aminomethyl fluorescein (0.1 g, 1.6×10 m$^{-4}$) and Na$_2$(PdCl$_4$) (0.12 g, 3.2×10$^{-4}$ m) were suspended in H$_2$O (90 cm$^3$) and heated under reflux for 30 minutes. The suspension was filtered whilst warm, resulting in a red/pink solution. A tarry dark red/brown residue was removed during filtration. The resulting solution is approximately 1.6 mM.

B. Preparation of Solution of Pd:Fluorexon in PVA 4 g of the solution prepared in A above was added to a commercial 6% PVA (16 g, Rhone Poulenc 25–140 Rhodoviol) in H$_2$O solution, and mixed in a high shear mixer for 5 minutes.

C. Production of Film 0.5 cm$^3$ of the mixture resulting from B above was drawn into a film on a polyester film sheet (Mylar) using a K-bar size 3, and left to dry at room temperature. A smooth film coating was formed, pale pink in colour.

D. Tests for Spoilage Products from Meat

A variety of tests were carried out on samples of fresh minced beef and chicken purchased from a local butcher. The samples were sub-divided and left with the existing natural flora. The samples were either refrigerated at 4° C. or stored at room temperature in closed vessels in which was located a 1 cm×1 cm label cut from the film produced as in C above.

E. Fluorescence Testing

E(i) Initial tests were carried out on a Fluorexon solution in water (a) and the Fluorexon solution immobilised in a film produced from 10% PVA in analogous manner to C above, and fluorescence peaks were determined. A distinct fluorescence peak at about 520 nm was seen for the solution and at about 530 nm for the film, demonstrating a slight shift because of the matrix of the film.

E(ii) Samples of the Pd:F solution prepared in A above were taken. One was retained as a control and other samples were admixed with 10$^{-6}$ M diethylamine. Fluorescence was measured at various times. It was readily seen that there was an increasing intensity with time, demonstrating the release of fluorescent ligand from the complex. Similar results have been obtained when the diethylamine was replaced with the amino-acid cysteine.

E(iii) The fluorescence of the labels used in the tests described in D above was established. In the case of the meat stored in the refrigerator at 24 hours, a very small peak was found for the film exposed to chicken breast, but there was no significant fluorescence from the film exposed to minced beef. However, by 168 hours, there was a dramatic increase in intensity in fluorescence in both cases. Both samples looked and smelled "spoilt" by this stage.

In the case of the meat stored at room temperature for 24 hours, both chicken breast and minced beef showed dramatic peaks at about 550 nm. The control of a label over sterile water did not show any corresponding peak. Although the intensity of the fluorescence from these meat labels is not so great as that resulting from seven days in the refrigerator, it is clear that the spoilage process has begun and that the Pd complex is being affected by spoilage products to release the fluorophore.

The invention claimed is:

1. A sensor for detecting a gaseous substance resulting from: (1) food spoilage within food packaging; (2) opening of the food packaging; or (3) compromise of the food packaging, the sensor comprising:

a film comprising a sensor composition, disposed on an internal surface of the food packaging or disposed on a label retained inside the food packaging, wherein said sensor composition comprises a resinous material and a metal co-ordinated complex, where in the metal is selected from the group consisting of palladium, platinum, ruthenium, and iron, and wherein the complex, upon exposure to the gaseous substance resulting from (1) food spoilage; (2) the opening of the food packaging; or (3) the compromise of the food packaging, undergoes a ligand exchange reaction by the binding of the gaseous substance to the metal(s) atom of the complex to release a component from the metal co-ordinated complex, creating a detectable change to the sensor.

2. A sensor according to claim 1, wherein the gaseous substance is selected from the group consisting of a sulfur-containing compound, a nitrogen-containing compound, an alcohol-containing compound, a carbonyl-containing compound, a phosphorus-containing compound, and mixtures thereof.

3. A sensor according to claim 1, wherein the metal is complexed with a chromophore or fluorophore.

4. A sensor according to claim 1, wherein the metal co-ordinated complex is a palladium-fluorophore complex.

5. A sensor according to claim 4, wherein the metal co-ordinated complex is palladium-Fluorexon.

6. A method of detecting a gaseous substance resulting from (1) food spoilage within a food packaging; (2) opening of the food packaging; or (3) compromise of the food packaging, comprising the step of:

applying a film comprising a sensor composition, to an internal surface of the food packaging or inserting a label coated with the film comprising the sensor composition to be retained within the packaging, wherein the sensor composition comprises a resinous material and a metal co-ordinated complex, where in the metal is selected from the group consisting of palladium, platinum, ruthenium, and iron, and which complex, upon exposure to the gaseous substance resulting from (1) food spoilage within the food packaging; (2) the opening of the food packaging; or (3) the compromise of the food packaging, undergoes a ligand exchange reaction by the binding of the gaseous substance to the metal(s) atom of the complex to release a component from the metal co-ordinated complex, creating a detectable change to the sensor.

7. A method according to claim 6, wherein the component released is a fluorophore or a chromophore released from the metal complex through the ligand exchange reaction with the gaseous substance.

8. A sensor according to claim 3, wherein the chromophore or fluorophore is selected from the group consisting of fluorescein isothiocyanate, fluorescein, fluorescein-amine, calcein blue, "Fura 2", quinzarin, alizarin complexone, alizarin red, alizarin, isocein, "Quin 2", and 4,4-dihydroxy-azobenzene 3,3-dicarboxylic acid disodium salt.

9. A sensor according to claim 1, wherein the resinous material is polyvinyl alcohol (PVA).

10. A sensor for detecting a gaseous substance resulting from food spoilage within a food packaging, comprising a metal co-ordinated complex disposed in or on a substrate, which complex, upon exposure to the gaseous substance resulting from food spoilage, undergoes a ligand exchange reaction by the binding of the gaseous substance to the metal of the complex to release a component from the metal co-ordinated complex, creating a detectable change to the sensor, wherein the metal complex is a palladium-fluorophore complex, and a barrier layer disposed between the metal complex and food disposed in the food packaging, wherein the barrier layer is permeable to the gaseous substance resulting from food spoilage but is not permeable to the metal or the released component.

11. A sensor according to claim 10, wherein the gaseous substance is selected from the group consisting of a sulfur-containing compound, a nitrogen-containing compound, an alcohol-containing compound, a carbonyl-containing compound, and a phosphorous-containing compound and mixtures thereof.

12. A sensor according to claim 10, wherein the metal co-ordinated complex is immobilized in a film.

13. A sensor according to claim 12, wherein the film is applied to a label adapted to be retained inside the food packaging.

14. A sensor according to claim 10, wherein the metal co-ordinated complex is palladium-Fluorexon.

15. A sensor according to claim 10, wherein the substrate is in the form of a film.

16. A sensor according to claim 1, wherein upon the release of the component, the sensor exhibits a color change, and the color change is only recognized when the sensor is excited by non-visible light.

17. A sensor according to claim 1, wherein upon the release of the component, the sensor exhibits a color change, and the color change is recognized under visible light.

18. A sensor according to claim 1, wherein the sensor comprises a plurality of sensors that individually indicate an increasing level of contamination up to a danger level.

19. A sensor according to claim 10 further comprising a resinous material.

20. A sensor according to claim 19, wherein the resinous material is polyvinyl alcohol (PVA).

21. A sensor according to claim 10, wherein the sensor is in the form of an adhesive label adapted to be adhered to the interior surface of a portion of the food packaging.

22. A sensor according to claim 10, wherein the substrate is polyester.

23. A sensor according to claim 10, wherein the food packaging is comprised of a packaging material and the metal complex is incorporated into the packaging material or into part of the packaging material.

24. A sensor according to claim 12, wherein the film is applied to the interior surface of a portion of the food packaging.

25. A method for detecting a gaseous substance resulting from food spoilage within a food packaging, comprising the step of:

applying to the interior of the food packaging a sensor comprising a metal co-ordinated complex, which complex, upon food spoilage, undergoes a ligand exchange reaction by the binding of the gaseous substance to the metal of the complex to release a component from the metal co-ordinated complex, creating a detectable change to the sensor, wherein the metal co-ordinated complex is a palladium-fluorophore complex.

26. A method according to claim 25, wherein the step of applying the sensor to the interior of the food packaging comprising applying the sensor to an internal surface of the food packaging and the method further comprises the step of providing a barrier layer disposed between the metal co-ordinated complex and the food, wherein the barrier layer is permeable to the gaseous substance resulting from food spoilage but not to the metal or the released component.

27. A method according to claim 25, wherein upon the release of the component, the sensor exhibits a color change, and the color change is recognized under visible light.

28. A method according to claim 25, wherein upon the release of the component, the sensor exhibits a color change, and the color change is recognized only when excited by non-visible light, and the method further comprises the step of exposing the sensor to non-visible light.

29. A method according to claim 25, wherein the sensor comprises a plurality of sensors that individually indicate an increasing level of the gaseous substance up to a danger level.

30. A method according to claim 25, wherein the step of applying the sensor to the interior of the food packaging comprises adhering the sensor to an interior surface of a portion of the food packaging.

31. A method according to claim 25, wherein the step of applying the sensor to the interior of the food packaging comprises incorporating the metal complex into a packaging material or into part of the packaging material.

32. A method according to claim 25, wherein the metal complex is immobilized in a film and the step of applying the sensor to the interior of the food packaging comprises applying the film to a label and inserting the label into the interior of the food packaging.

33. A sensor according to claim 1, wherein the sensor composition undergoes a complete color change at a predetermined level of gaseous substance as a result of the ligand exchange reaction.

34. A method according to claim 25, wherein the sensor composition undergoes a complete color change at a predetermined level of gaseous substance as a result of the ligand exchange reaction.

35. A method according to claim 25, wherein the sensor further comprises a resinous material.

36. A method according to claim 25, wherein the sensor is applied to the interior of the food packaging in the form of an ink.

37. A method according to claim 36, wherein the step of applying the sensor to the interior of the food packaging comprises applying the ink to a label and inserting the label into the interior of the food packaging.

38. A method according to claim 36, wherein the ink comprises an ink component selected from the group consisting of a drier, a plasticizer, a filler, a surfactant, a pigment, and mixtures thereof.

* * * * *

UNITED STATES PATENT AND TRADEMARK OFFICE
CERTIFICATE OF CORRECTION

PATENT NO. : 7,153,532 B1 Page 1 of 1
APPLICATION NO. : 09/763981
DATED : December 26, 2006
INVENTOR(S) : Elsome et al.

It is certified that error appears in the above-identified patent and that said Letters Patent is hereby corrected as shown below:

Column 5, line 35, delete "where in" and insert therefor --wherein--.

Column 6, line 64, delete "comprising" and insert therefor --comprises--.

Signed and Sealed this

Fourteenth Day of August, 2007

JON W. DUDAS
*Director of the United States Patent and Trademark Office*